United States Patent [19]

Kolar et al.

[11] Patent Number: 5,091,521

[45] Date of Patent: Feb. 25, 1992

[54] CIS-PLATINUM COMPLEXES, A PROCESS FOR THE PREPARATION THEREOF, AND PHARMACEUTICALS CONTAINING THESE COMPOUNDS

[75] Inventors: Cenek Kolar; Konrad Dehmel; Hans Peter Kraemer, all of Marburg, Fed. Rep. of Germany

[73] Assignee: Behringwerke Aktiengesellschaft, Marburg/Lahn, Fed. Rep. of Germany

[21] Appl. No.: 576,185

[22] Filed: Aug. 28, 1990

Related U.S. Application Data

[63] Continuation of Ser. No. 467,276, Jan. 24, 1990, abandoned, which is a continuation of Ser. No. 93,207, Sep. 4, 1987, abandoned.

[30] Foreign Application Priority Data

Sep. 8, 1986 [DE]  Fed. Rep. of Germany ....... 3630497

[51] Int. Cl.$^5$ ..................... A61K 31/28; C07C 93/04; C07C 103/44; C07C 117/00; C07H 15/04
[52] U.S. Cl. .................. 536/17.1; 549/377; 556/137; 514/908
[58] Field of Search ....... 536/17.1; 549/377; 556/137; 514/908

[56]  References Cited

U.S. PATENT DOCUMENTS 4,659,810  4/1987  Thiem et al. .................... 536/124

FOREIGN PATENT DOCUMENTS

| | | |
|---|---|---|
| 0098135A2 | 1/1984 | European Pat. Off. . |
| 3337333A1 | 4/1984 | Fed. Rep. of Germany . |
| 3432320A1 | 3/1986 | Fed. Rep. of Germany . |
| 62-59294 | 3/1987 | Japan . |
| 856695 | 4/1986 | South Africa . |
| 2024823A | 1/1980 | United Kingdom . |
| 2128615A | 5/1984 | United Kingdom . |

OTHER PUBLICATIONS

Prestayko et al., Cisplatin; Current Status and New Developments, Academic Press, 1980, pp. 149-191.
Kraemer et al., A Modified Screening System to Select New Cytostatic Drugs, Behring Inst. Mitt., No. 74, (1984), pp. 301-328.

Primary Examiner—Ronald W. Griffin
Attorney, Agent, or Firm—Finnegan, Henderson, Farabow, Garrett, and Dunner

[57]  ABSTRACT

Compounds of the general formula I

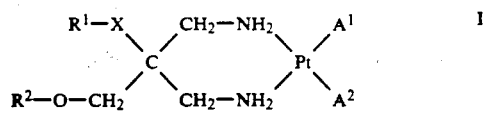

in which
$R^1$ represents a hydrogen atom or an alkyl group of the formula $CH_3(CH_2)_n$—where $n=0$ to 5,
$R^2$ represents a hydrogen atom when X is a carbamoyl group, an alkyl group having 1 to 6 carbon atoms, a group, bonded in an ether-like fashion, of the formula $R^3$—O—$CH_2$—$(CHR^4)_m$—$CH_2$— in which
$R^3$ is a hydrogen atom or an alkyl group having 1 to 6 carbon atoms,
$R^4$ is a hydroxyl group or an alkyloxy group having 1 to 3 carbon atoms, and m is 0 to 2, represents a group, bonded in an ether-like fashion, of the formula H—$(CH_2)_a$—(O—$(CH_2)_b)_c$— where $a=0$ to 4, $b=1$ to 4 and $c=1$ to 7, or
$R^2$ represents a radical, bonded in a O-glycoside fashion of the formula

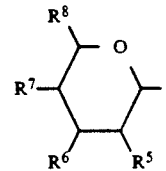

in which
$R^5$, $R^6$ and $R^7$, independently of one another, are a hydrogen atom or a hydroxyl group, and
$R^8$ is a hydrogen atom, a methyl group or a hydroxy methyl group,
X represents a methylene group or a carbamoyl group or a covalent bond between $R^1$ and the 2-carbon atom,
$A^1$ and $A^2$ are indentical and represent the hydroxyl group, chloride, bromide, iodide, nitrate, acetate or trifluoroacetate, or
$A^1$ represents sulfate or carbonate and $A^2$ represents $H_2O$ or
$A^1$ and $A^2$ together represent the dianion of an organic acid such as oxalic, malonic, hydroxymalonic, ethylmalonic, 1,1- or 1,2-cyclobutanedicarboxylic, phthalic, 3- or 4-carboxyphthalic, 3,4-dicarboxyphthalic or N-(carbamoylmethyl)-iminodiacetic acid, are described, and also a process for the preparation thereof, and a medicament containg these compounds.

13 Claims, No Drawings

CIS-PLATINUM COMPLEXES, A PROCESS FOR THE PREPARATION THEREOF, AND PHARMACEUTICALS CONTAINING THESE COMPOUNDS

This application is a continuation of application Ser. No. 07/467,276, filed Jan. 24, 1990, which is a continuation of application Ser. No. 07/093,207, filed Sept. 4, 1987, both now abandoned.

The invention relates to novel cis-platinum complex compounds containing a propane-1,3-diamine derivative as ligand, a process for the preparation thereof, and a pharmaceutical containing these novel compounds.

Cis-platinum complexes of the general formula cis-$L_2PtX_2$ where L is a neutral ligand, such as $NH_3$ or an organic amine, and X is an anionic ligand, such as chloride or an anion of an organic acid, have an antitumoral activity (Cisplatin; Current Status and New Developments, eds. A. W. Prestayko, S. T. Crooke and S. K. Carter, Academic Press, 1980, 149-191).

Cis-diamminedichloroplatinum(II) has been introduced as a medicament.

EPA 0,098,135 (A2) describes cis-platinum complexes which contain, as ligands, alkyl- or hydroxyalkyl-substituted propane-1,3-diamine derivatives. DE 3,337,333 (A1) and GB 2,024,823 (A) likewise describe (alkyl-, aryl- or aryl-alkylpropane-1,3-diamine)platinum complexes.

DE 3,432,320 (A1) describes symmetrical (propane-1,3-diamine)platinum complexes which carry two alkyloxymethyl substituents on carbon 2.

The kidney and bone marrow toxicity of alkyl-diaminoplatinum complexes and their low solubility are disadvantageous.

Surprisingly, it became apparent that the previously unobtainable synthetic compounds N,N-(2-ethyl-2-methoxymethylpropane-1,3-diamine)dichloroplatinum-(II) and the corresponding malonate derivative have a high cytostatic activity in the "in vivo" test using the L1210 tumor cell line, and that these compounds are only partially cross resistant in vitro to the medicament cis-diamminedichloroplatinum(II) which has been introduced for hospital use.

Proceeding from this knowledge, the object of the present invention was to prepare novel (propane-1,3-diamine)platinum complexes which are asymmetrically substituted at the 2-carbon atom, and to investigate the pharmacological utility thereof as cytostatics.

This object was achieved by the compounds of the formula I, which were conspicuous in the test for cytostatic activity.

The invention relates to cis-diamineplatinum(II) complexes of the formula I

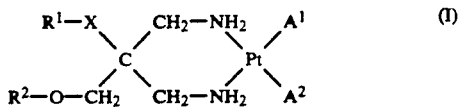

(I)

in which $R^1$ represents a hydrogen atom or an alkyl group of the formula $CH_3(CH_2)_n$— where n = 0 to 5, $R^2$ represents a hydrogen atom when X is a carbamoyl group, an alkyl group having 1 to 6 carbon atoms, a group, bonded in an ether-like fashion, of the formula $R^3$—O—$CH_2$—$(CHR^4)_m$—$CH_2$—in which $R^3$ is a hydrogen atom or an alkyl group having 1 to 6 carbon atoms, $R^4$ is a hydroxyl group or an alkyloxy group having 1 to 3 carbon atoms, and m is 0 to 2, represents a group, bonded in an ether-like fashion, of the formula H—$(CH_2)_a$—(O—$(CH_2)_b)_c$—where a = 0 to 4, b = 1 to 4 and c = 1 to 7, or $R^2$ represents a radical, bonded in a O-glycoside fashion, of the formula

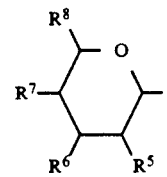

in which $R^5$, $R^6$ and $R^7$, independently of one another, are a hydrogen atom or a hydroxyl group, and $R^8$ is a hydrogen atom, a methyl group or a hydroxy methyl group, X represents a methylene group or a carbamoyl group or a covalent bond between $R^1$ and the 2-carbon atom, $A^1$ and $A^2$ are identical and represent the hydroxyl group, chloride, bromide, iodide, nitrate, acetate or trifluoroacetate, or $A^1$ represents sulfate or carbonate and $A^2$ represents $H_2O$ or $A^1$ and $A^2$ together represent the dianion of an organic acid such as oxalic, malonic, hydroxymalonic, ethylmalonic, 1,1- or 1,2-cyclobutanedicarboxylic, phthalic, 3- or 4-carboxyphthalic, 3,4-dicarboxyphthalic or N-(carbamoylmethyl)-iminodiacetic acid.

In the context of the invention, preferred compounds of general formula I are those in which the radicals $R^1$—X are a methyl or ethyl group, $R^2$ is a methyl or ethyl group, a group, bonded in an ether-like fashion, of the formula

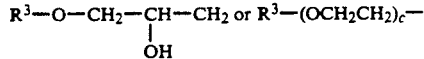

where $R^3$ is a hydrogen atom or a methyl radical, and c = 1, 2, 3 or 6, or $R^2$ is a radical, bonded in a O-glycoside fashion, of the formula

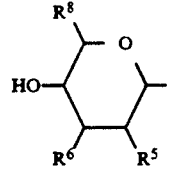

where $R^5$ and $R^6$, independently of one another, are a hydrogen atom or a hydroxyl group, $R^8$ is a hydrogen atom, a methyl group or a hydroxymethyl group, $A^1$ and $A^2$ are identical and are the hydroxyl group, chloride or nitrate, or $A^1$ and $A^2$ together are the dianion of malonic, 1,1-cyclobutane-dicarboxylic or N-(carbamoylmethyl)-iminodiacetic acid, and compounds of the general formula I in which the radicals $R^1$—X are an acetamido group, and $R^2$ is a hydrogen atom, and $A^1$ and $A^2$ have the lastmentioned meaning.

The compounds of the formula I according to the invention can be prepared, starting from a compound of the formula II

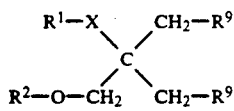

in which $R^1$ is a hydrogen atom or an alkyl group of the formula $CH_3(CH_2)_n$, where n=0 to 5, $R^2$ is a hydrogen atom, $R^9$ is an azido group, and X is a methylene group or a carbamoyl group or a covalent bond between $R^1$ and the 2-carbon atom, in a fashion which is known per se by preparing an ether or glycoside derivative of the formula II in which $R^1$, $R^9$ and X retain their abovementioned meaning and $R^2$ is an alkyl group having 1 to 6 carbon atoms, a group, bonded in an ether-like fashion, of the formula $R^3$—O—$CH_2$—$(CHR^4)_m$—$CH_2$— in which $R^3$ is a hydrogen atom or an alkyl group having 1 to 6 carbon atoms, $R^4$ is a hydroxyl group or an alkyloxy group and m is 0 to 2, or a group, bonded in an ether-like fashion, of the formula H—$(CH_2)_a$—$(O$—$(CH_2)_b)_c$— where a=0 to 4, b=1 to 4 and c=1 to 7, or $R^2$ is a radical, bonded in an O-glycoside fashion, of the formula

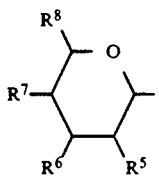

in which $R^5$, $R^6$ and $R^7$, independently of one another, are a hydrogen atom or a hydroxyl group, or $R^5$ and $R^6$ represent an electron pair, and $R^8$ is a hydrogen atom, a methyl group or a hydroxy methyl group, and hydrogenating the derivative obtained in the presence of palladium/charcoal and an organic solvent, such as methanol, ethyl acetate or dioxane, a diamino compound being formed, which is reacted in a fashion which is known per se with $K_2PtCl_4$ to form a platinum complex of the formula I, from which further derivatives of the formula I are subsequently prepared.

The preparation of a compound of the general formula I is based on the use of processes which were described, for example in German Offenlegungsschrift 3,432,320 or are customary in carbohydrate chemistry.

Their cytostatic activity was determined in vitro on L1210 leukemia cells of the mouse or in vivo on L1210 leukemia, B16 melanoma and Lewis lung adenocarcinoma. The acute toxicity of the compounds was determined on NMRI mice. Taking into account the low acute toxicity (H. P. Kraemer, H. H. Sedlacek, Behring Institute Mitt. 74, 301-328, 1984), the compounds according to the invention proved to be superior to cisplatin with respect to cytotoxicity, solubility and activity on L1210 leukemia. In addition, the compounds according to the invention are also active in the case of tumor cells which are resistant towards cis-platin.

The invention also relates to medicaments, preferably for tumor therapy, which contain an active amount of one or more of the compounds of the formula I as active ingredient.

The manner of dosage and administration essentially corresponds to that which is known for cis-$(NH_3)_2PtCl_2$, and higher dosages and/or more frequent administration are also suitable due to the favorable therapeutic index of the compounds according to the invention.

Besides conventional pharmaceutical formulation agents and/ or diluents, these medicaments can also contain, if appropriate, further active ingredients, besides the compounds of the formula I, for supplementing the therapy, so long as these do not exhibit any undesired side effects together with the compounds of the formula I according to the invention.

EXAMPLES

The present invention is described in greater detail in the following examples, without these representing a limitation.

EXAMPLE 1

Preparation of 1,3-diazidopropane derivatives 2,2-Bis-(azidomethyl)-propan-1-ol (compound 1)

150 g (1.25 mol) of 2-hydroxymethyl-2-methylpropane-1,3-diol were dissolved in 1.5 liters of pyridine, and 487 g (2.5 mol) of p-toluenesulfonyl chloride were added. After stirring at room temperature for 18 hours, the reaction batch was concentrated in a water-pump vacuum (in vacuo) and distilled twice with toluene. The residue was taken up in chloroform, and the solution was washed three times with ice water. The organic phase was concentrated to dryness in vacuo, and the residue was purified by chromatography over 2000 g of silica gel (eluent: dichloromethane/ethyl acetate). The resultant product (245 g) was dissolved in 1 liter of DMF, and a 76.5 g (1.17 mol) of sodium azide were added. The reaction batch was stirred at 110° C. for 12 hours. The reaction mixture was concentrated to dryness in vacuo, and the residue was dissolved in ethyl acetate, and the water-soluble components were removed by washing by shaking three times with water. The organic phase was concentrated to dryness in vacuo, and the resultant residue was purified by column chromatography over 1500 g of silica gel (eluent: petroleum ether/toluene/ethyl acetate 20:10:1).

Yield: 79.8 g (83%).

IR (cm$^{-1}$, $N_3$): 2100.

$^{13}C$ NMR (90 MHz, $CDCl_3$, delta): 65.58 ($CH_2OH$), 55.37 (2×$CH_2N$), 40.64 (C), 14.47 ($CH_3$).

2,2-bis-(azidomethyl)-butan-1-ol (compound 2)

Starting from 2-ethyl-2-hydroxymethylpropane-1,3-diol, compound 2 was prepared according to the directions for the synthesis of compound 1.

IR (cm$^1$, $N_3$): 2100.

2-Acetamido-2,2-bis-(azidomethyl)-ethanol (compound 3)

100 g (0.82 mol) of tris-hydroxymethylaminomethane were dissolved in 600 ml of pyridine, and 790 ml of acetic anhydride were added at $-20°$ C. After stirring at room temperature for 10 hours, the reaction batch was worked up in a conventional manner. The resultant tetraacetyl derivative (181 g) was dissolved in methanol, and a catalytic amount of sodium methylate was added at $0°$ C. After 3 hours, the mixture was neutralized using DOWEX WX8 and concentrated to dryness. The product, trishydroxymethylacetamidomethane, was converted into compound 3 according to the directions for the preparation of compound 1.

IR $(cm^{-1})$ 2100, 1660.

$^{13}$C NMR (90 MHz, CDCl$_3$, delta): 168.18 (CONH), 75.04 (C), 72.65 (CH$_2$OH), 56.24 (2xCH$_2$N$_3$), 14.35 (CH$_3$).

Example 2

Alkylation and glycosidization of compounds 1 and 2.

2,2-Bis-(azidomethyl)-propyl methyl ether (compound 4)

7.3 g (43 mmol) of compound 1 were dissolved in 50 ml of dioxane, and 7.2 g of potassium tert.-butylate were added. 6.71 g (47 mmol) of methyl iodide, dissolved in 20 ml of dioxane, were added dropwise to the mixture. After stirring at room temperature for 3 hours, the reaction batch was concentrated in vacuo. The resultant syrup was purified by chromatography over 70 g of silica gel (eluent: hexane/diisopropyl ether 5:1).

Yield: 6.3 g (80%)

Elemental analysis: Calc. C 39.12 H 6.56 N 45.62. Found C 39.06 H 6.52 N 45.32.

$^{13}$C NMR (90 MHz, CDCl$_3$, delta): 75.74 (CH$_2$O), 59.65 (CH$_3$O), 56.29 (2×CH$_2$N$_3$), 41.61 (C), 18.96 (CH$_3$).

2,2-Bis-(azidomethyl)-butyl methyl ether (compound 5)

Starting from compound 2, compound 5 was prepared according to the directions for the synthesis of compound 4.

IR $(cm^{-1}, N_3)$: 2100.

$^{13}$C NMR (90 MHz, CDCl$_3$, delta): 72.76 (CH$_2$O), 58.89 (CH$_3$O), 53.20 (2×CH$_2$N$_3$), 43.12 (C), 23.40 (CH$_2$), 7.1 (CH$_3$).

2,2-Bis-(azidomethyl)-propyl 2',3'-dihydroxypropyl ether (compound 6)

15 g (88 mmol) of compound 1 were dissolved in 200 ml of DMF, and 9.9 g (176 mmol) of KOH were added. 24 g (176 mmol) of epibromohydrin, dissolved in 50 ml of DMF, were added dropwise within 1 hour. After stirring at room temperature for 24 hours, the reaction batch was filtered and concentrated in vacuo to a syrup. The product was then purified by chromatography over 500 g of silica gel (eluent: dichloromethane/petroleum ether/ethyl acetate 1:1:0.1). The resultant glycidyl ether derivative was emulsified in dioxane/water 1:1 and hydrolysed to compound 6 using KOH at $70°$ C. After neutralization with hydrochloric acid, the batch was concentrated, dissolved in ethyl acetate and stirred with 20 g of sodium sulfate. After filtration and evaporation of the organic phase, the residue was purified by chromatography (200 g of silica gel, eluent: dichloromethane/acetone 6:1).

Yield: 16.3 g (76%)

$^{13}$C NMR (90 MHz, CDCl$_3$, delta): 74.55 (CH$_2$), 73.25 (CH$_2$), 71.24 (CHOH), 64.42 (CH$_2$OH), 56.29 (2xCH$_2$N$_3$), 41.55 (C), 19.07 (CH$_3$). IR $(cm^{-1}, N_3)$: 2100.

2,2-Bis-(azidomethyl)-propyl 2'-hydroxy-3'-methoxypropyl ether (compound 7)

The glycidyl ether derivative (4 g), as described in the preparation of compound 6, was dissolved in dry methanol and cleaved at room temperature using solid KOH (2 g). The resultant methoxy compound 7 was subsequently filtered over silica gel.

Yield: 4.3 g (99%)

IR $(cm^{-1}, N_3)$: 2100

$^{13}$C NMR (90 MHz), CDCl$_3$, delta): 74.44 (2×CH$_2$), 73.14 (CH), 69.83 (CH$_2$), 59.76 (OCH$_3$), 56.29 (2×CH$_2$N$_3$), 41.66 (C), 19.07 (CH$_3$).

2,2-Bis-(azidomethyl)-propyl-2,3-didesoxy-alpha-D-erythro-hex-2-enopyranoside (compound 8) and 2,2-bis-(azidomethyl)-propyl-2-desoxy-alpha-D-arabinohexopyranoside (compound 9)

7.5 g (44 mmol) of compound 1 were taken up in 250 ml of dioxane. After addition of 12 g (44 mmol) of 3,4,6-tri-O-acetyl-D-glucal and 0.960 g (4.4 mmol) of p-toluenesulfonic acid, the reaction batch was stirred at $70°$ C. for 20 hours. The mixture was then concentrated and worked up as customary. Two compounds were obtained after separation by column chromatography: 2,2-bis-(azidomethyl)-propyl-4,6-di-O-acetyl-2,3-didesoxy-alpha-D-erythrohex-2-enopyranoside (7 g =40%) and 2,2-bis-(azidomethyl)-propyl-3,4,6-tri-O-acetyl-alpha-D-arabinohexopyranoside (3.5 g =21%). Both compounds were deacetylated using sodium methylate, as customary.

Compound 8

Yield: 3.2 g

IR $(cm^{-1}, N_3)$: 2100.

$^{13}$C NMR (90 MHz, CDCl$_3$, delta): 134.09 (CH; C-2), 126.18 (CH; C-3), 95.08 (CH C-1), 72.22 (CH$_2$), 71.19 (CH), 64.20 (CH$_2$), 62.79 (CH), 56.18 (2x CH$_2$N$_3$), 41.28 (C), 19.02 CH$_3$).

Compound 9

Yield: 2.7 g

IR $(cm^{-1}, N_3)$: 2100.

$^{13}$C NMR (90 MHz, CDCl$_3$, delta): 98.72 (CH, C-1), 72.54 (CH), 72.38 (CH), 70.54 (CH), 69.68 (CH$_2$), 62.25 (CH$_2$), 56.19 (2×CH$_2$N$_3$), 41.28 (CH$_2$), 37.92 (C), 19.23 CH$_3$) 1H NMR (90 MHz, CDCl$_3$, delta): 4.78 (1-H;J(1.2) =1.2 Hz, J (1.2')=2 Hz).

2,2-Bis-(azidomethyl)-propyl-$\beta$-D-glucopyranoside (compound 10)

3.75 g (22 mmol) of compound 1 were dissolved in 60 ml of toluene/nitromethane 1:1. After addition of 5.5 g (72 mmol) of mercury of cyanide and 9.1 g (22 mmol) of acetobromoglucose, the reaction mixture was warmed to $40°$ C., 10% by volume of the reaction solution being removed by distillation under reduced pressure.

After 14 hours, chloroform was added to the batch, which was then washed twice with a 10% strength KI solution, once with 1% strength sodium hydrogen carbonate solution and once with ice water. After drying using sodium sulfate, the batch was concentrated to dryness in vacuo, and the residue was purified by column chromatography. The resultant compound was deacetylated in the presence of sodium methylate.

Yield: 5.9 g (82%).

Elemental analysis: Calc. C 39.75 H 6.06 N 25.29. Found C 39.82 H 6.05 N 25.13.

IR (cm$^{-1}$, N$_3$): 2100.

Example 3

Preparation of diamino ligands and complexing thereof with potassium tetrachloroplatinate N,N'-(2-methoxymethyl-2-methyl-1,3-propanediamine)dichloro-platinum(II) (compound 11)

4.8 g (26.05 mmol) of compound 4 were dissolved in 30 ml of a mixture of methanol and ethyl acetate 3:1. After addition of 3 g of Pd/C, (10%), the reaction batch was hydrogenated for 2 hours at room temperature with stirring. The course of the hydrogenation was followed by thin-layer chromatography. After filtering off the catalyst, the solution was evaporated to dryness. The resultant product, which exhibited no azido band in the IR spectrum, was employed without further purification steps in the following reaction with platinum salts.

Yield: 3 g (88%).

3 g (22.7 mmol) of the diamino intermediate were dissolved in methanol and added to 50 ml of an aqueous solution of 9.4 g (22.7 mmol) of K$_2$PtCl$_4$. After stirring for 18 hours at room temperature, the precipitated reaction product was filtered off and washed several times with ice water. The combined filtrates were evaporated in vacuo to a volume of 15 ml, when the reaction product had reprecipitated.

Yield: 6 g (68%).

Elemental analysis: Calc. C 18.10, H 4.05, Cl 17.8, N 7.03, Pt 49.0. Found C 18.50, H 4.00, Cl 17.3, N 6.91, Pt 48.5. IR (cm$^{-1}$): 3500, 3250, 3150, 2950, 2930, 2880, 2770, 1575, 1450.

N,N'-(2-ethyl-2-methoxymethyl-1,3-propanediamine)-dichloro-platinum(II) (compound 12)

Compound 12 was prepared according to the directions for the synthesis of compound 11. 9.3 g (46.5 mmol) of compound 5 were hydrogenated, and the diamino intermediate was reacted with 19.3 g (46.5 mmol) of K$_2$PtCl$_4$ to give compound 12.

Elemental analysis: Calc. C 20.40, H 4.40, Cl 17.19, N 6.79, Pt 47.32. Found C 20.24, H 4.61, Cl 17.50, N 6.50, Pt 46.80.

N,N'-(2-(2',3'-dihydroxypropyloxymethyl)-2-methyl-1,3-propanediamine)dichloroplatinum(II) (compound 13)

Compound 13 was prepared according to the directions for the synthesis of compound 11.

7.5 g (30.7 mmol) of compound 6 were hydrogenated, and the resultant diamino intermediate was reacted with 12.7 g (30.7 mmol) of K2PtCl4 to give compound 13.

Yield: 7.2 g (52%)

Elemental analysis: Calc. C 20.69, H 4.39, Cl 15.47, N 6.14, Pt 42.57. Found C 20.32, H 4.21, Cl 15.17, N 6.01, Pt 41.73.

$^{13}$C NMR (90 MHz, D$_2$O, delta, dioxane standard): 80.63, 74.48, 72.39, 65.08, 52.79 (CH$_2$NH$_2$), 39.37, 20.95.

N,N'-(2-(2'-hydroxy-3'-methoxypropyloxymethyl)-2-methyl-1,3-propanediamine)dichloroplatinum(II) (compound 14)

Compound 14 was prepared by the process for the synthesis of compound 11 starting from compound 7.

Elemental analysis: Calc.: C 22.88, H 4.69, Cl 15.01, N 5.93, Pt 41.30. Found: C 23.40, H 4.61, Cl 15.20, N 5.81, Pt 41.10.

$^{13}$C NMR (90 MHz, D$_2$O, delta, dioxane standard): 80.96, 75.56, 74.48, 70.48, 60.64, 52.70 (2×CH$_2$NH$_2$), 39.05, 21.27.

N,N'-(2-(2',3'-didesoxy-alpha-D-erythrohexopyranosyloxy-methyl)-2-methyl-1,3-propanediamine)-dichloroplatinum(II) (compound 15)

9 g (30.30 mmol) of compound 8 were hydrogenated in the presence of 4 g of Pd/C (10%) and 200 ml of methanol. The resultant compound was reacted, as described above, with 12.0 g (30.30 mmol) of K$_2$PtCl$_4$ to give compound 15.

Yield: 7 g (45%).

$^{13}$C NMR (90 MHz, DMF, delta): 97.46, 76.55, 73.08, 67.18, 63.50, 50.98, 50.60, 39.44, 30.99, 28.39, 19.93.

N,N'-(2-(8-D-glucopyranosyloxymethyl)-2-methyl-1,3-propane-diamine)dichloroplatinum(II) (compound 16)

3.32 g (10 mmol) of compound 10 were hydrogenated in the presence of Pd/C, and the resultant diamine was reacted with K$_2$PtCl$_4$ to compound 16.

Yield: 4.9 g (89%).

Elemental analysis: Calc.: C 24.17, H 4.42, Cl 12.97, N 5.12, Pt 35.72. Found: C 24.03, H 4.41, Cl 12.38, N 5.01, Pt 35.20.

N,N'-(2-acetamido-2-hydroxymethyl-1,3-propanediamine)di-chloroplatinum(II) (compound 17)

2.8 g (14.07 mmol) of compound 3 were hydrogenated in the presence of Pd/C, and the diamino product was reacted with K$_2$PtCl$_4$ to give compound 17.

Yield: 3.19 g (55%)

Elemental analysis: Calc.: C 16.86, H 3.54, Cl 16.59, N 9.83, Pt 45.66. Found: C 17.00, H 3.50, Cl 16.60, N 9.90, Pt 46.10.

$^{13}$C NMR (90 MHz, DMF, delta): 169.79 (CO), 83.84 (CH$_2$OH), 64.20 (C), 51.11 (CH$_2$N), 48.78 (CH$_2$N), 14.82 (CH$_3$).

Example 4

Compounds 11 to 17, which exist as platinum(II) dichloride derivatives, were converted into their nitrate, hydroxyl and carboxylic acid derivatives according to the following equation.

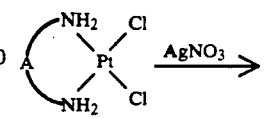

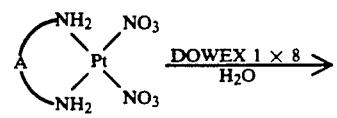

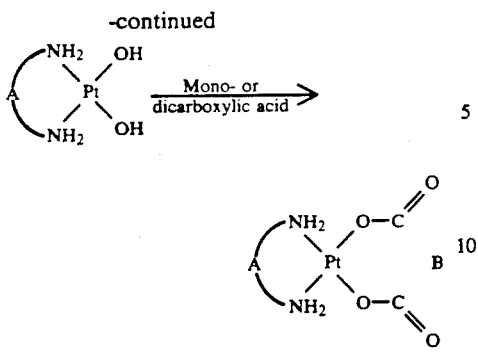

a) Preparation of platinum complexes with nitrate as ligands 10 mmol of platinum(II) dichloride derivatives were suspended in 100 ml of distilled, degassed water. After addition of 20 mmol of a silver nitrate, dissolved in 50 ml of water, the reaction batch was stirred at room temperature for 25 hours with exclusion of light. The course of the reaction was followed by thin-layer chromatography on cellulose (13255, Messrs. Eastman, eluent: butanol/glacial acetic acid/water 5:3:2) and by means of HPLC (RP18 lichrosorb 7 μ250×4, eluent: methanol/water gradient, detection: UV 220 nm). After filtering off the precipitated silver chloride, the nitrate derivative, dissolved in water, was employed in the following reaction without further purification steps.

b) Preparation of platinum complexes having hydroxyl groups as ligands 10 g of ion exchanger resin (DOWEX, type 1×8; activation ion with 10N NaOH) were added with stirring to the solution containing the dinitrate intermediate. After 30 minutes, the thin-layer chromatogram (n-butanol/glacial acetic acid/water 5:3:2; cellulose film (13255 Messrs. Eastmann)) showed that replacement of the nitrate by hydroxyl groups had proceeded to completion. After filtering off the resin, the filtrate was concentrated to dryness in vacuo with exclusion of light.

c) Preparation of platinum complexes with carboxylic acid as ligand or ligands 10 mmol of the dihydroxyplatinum(II) compound were dissolved in 50 ml of distilled, degassed water. 10 mmol of di- or oligocarboxylic acid, dissolved in 20 ml of water, were added to this solution with stirring and exclusion of light. After 6 hours, the reaction solution was evaporated to dryness in vacuo. The product was recrystallized from water/methanol.

The following compounds were prepared as described in Example 4a:

N,N'-(2-methoxymethyl-2-methyl-1,3-propanediamine)platinum(II) dinitrate (compound 18)

Compound 18 was prepared starting from compound 11.

N,N'-(2-ethyl-2-methoxymethyl-1,3-propanediamine)-platinum(II) dinitrate (compound 19)

Compound 19 was prepared starting from compound 12.

N,N'-(2-(2',3'-dihydroxypropyloxymethyl)-2-methyl-1,3-propanediamine)platinum(II) dinitrate (compound 20)

Compound 20 was prepared starting from compound 13.

N,N'-(2-(2'-hydroxy-3'-methoxy-propyloxymethyl)-2-methyl-1,3-propanediamine)platinum(II) dinitrate (compound 21)

Compound 21 was prepared starting from compound 14.

N,N'-(2-(2',3'-didesoxy-alpha-D-erythrohexopyranosyloxy-methyl)-2-methyl-1,3-propanediamine)-platinum(II) dinitrate (compound 22)

Compound 22 was prepared starting from compound 15.

N,N'-(2-(β-0-glucopyranosyloxymethyl)-2-methyl-1,3-propane-diamine)platinum(II) dinitrate (compound 23)

Compound 23 was prepared starting from compound 16.

The following compounds were prepared as described in Example 4b:

N,N'-(2-methyloxymethyl-2-methyl-1,3-propanediamine)-platinum(II) hydroxide (compound 24)

Compound 24 was prepared starting from compound 18.

Elemental analysis: Calc.: C 19.93, H 5.01, N 7.75, Pt 54.02. Found: C 19.57, H 5.06, N 7.37, Pt 53.72.

N,N'-(2-ethyl-2-methoxymethyl-1,3-propanediamine)-platinum (II) hydroxide (compound 25)

Compound 25 was prepared starting from compound 19. HPLC (RP-8, 7μ, water, UV 220 nm), retention time: 2.34 minutes.

Elemental analysis: Calc.: C 22.37, H 5.36, N 7.46, Pt 51.96. Found: C 22.18, H 5.38, N 7.22, Pt 51.36.

N,N'-(2-(2',3'-dihydroxypropyloxymethyl)-2-methyl-1,3-propanediamine)platinum(II) hydroxide (compound 26)

Compound 26 was prepared starting from compound 20.

Elemental analysis: Calc.: C 22.79, H 5.26, N 6.64, Pt 46.31. Found: C 22.61, H 5.17, N 6.51, Pt 45.95.

N,N'-(2-(2'-hydroxy-3'-methoxypropyloxymethyl)-2-methyl-1,3-propanediamine)platinum(II) hydroxide (compound 27)

Compound 27 was prepared starting from compound 21

Elemental analysis: Calc.: C 24.82, H 5.55, N 6.43, Pt 44.82. Found: C 24.79, H 5.58, N 6.32, Pt 44.37.

N,N'-(2-(2',3'-didesoxy-alpha-D-erythrohexopyranosyloxy-methyl)-2-methyl-1,3-propanediamine)-platinum(II) hydroxide (compound 28)

Compound 28 was prepared starting from compound 22.

Elemental analysis: Calc.: C 27.66, H 5.48, N 5.86, Pt 40.87. Found: C 27.73, H 5.47, N 5.83, Pt 40.61.

N,N'-(2-(β-O-glucopyranosyloxymethyl)-2-methyl-1,3-propane-diamine)platinum(II) hydroxide (compound 29)

Compound 29 was prepared starting from compound 23.

Elemental analysis: Calc.: C 25.92, H 5.14, N 5.50, Pt 38.31. Found: C 25.81, H 5.03, N 5.31, Pt 38.09.

The following compounds were prepared as described in Example 4c:

N,N'-(2-methyloxymethyl-2-methyl-1,3-propanediamine)platinum(II) malonate (compound 30)

Compound 30 was prepared starting from compound 24. HPLC (RP-8, 7μ, eluent: water/methanol 85:15, UV 220 nm): Retention time 5.12 minutes. $^{13}$C NMR (90 MHz, D$_2$O, delta): 181.34 (COO), 81.39 (CH$_2$), 61.34 CH$_3$O), 53.02 (2×CH$_2$N), 50.16 (CH$_2$), 40.45 (C), 20.76 CH$_3$).

N,N'-(2-methyloxymethyl-2-methyl-1,3-propanediamine)platinum(II)
1,1-cyclobutanedicarboxylate (compound 31)

Compound 31 was prepared starting from compound 24. HPLC (RP-8, 7μ, water, UV 220 nm): Retention time 7.7 minutes. $^{13}$C NMR (90 MHz, D$_2$O, delta): 184.78 (COO), 81.38 (CH$_2$), 61.72 CH$_3$), 58.80 (C), 53.35 (2×CH$_2$N), 40.64 (C), 33.78 (CH$_2$), 33.33 (CH$_2$), 20.95 CH$_3$), 17.78 (CH$_2$).

Elemental analysis: Calc.: C 30.69, H 4.72, N 5.96, Pt 41.57. Found: C 30.87, H 4.83, N 5.71, Pt 41.08.

N,N'-(2-ethyl-2-methyloxymethyl-1,3-propanediamine)platinum(II)
1,1-cyclobutanedicarboxylate (compound 32)

Compound 32 is prepared starting from compound 25.
HPLC (RP-8, 7μ, water/methanol 95:5, UV 220): Retention time 17.61 minutes.

$^{13}$C NMR (90 MHz, D$_2$O, delta): 184.77 (COO), 79.37 (CH$_2$), 61.91 (CH$_2$), 59.37 (C), 51.81 (CH$_2$N), 51.69 (CH$_2$N), 43.30 (C), 34.16 (CH$_2$), 33.97 (CH$_2$), 27.81 CH$_3$), 18.41 (CH$_2$), 9.46 CH$_3$).

Elemental analysis: Calc.: C 35.85, H 5.50, N 6.43, Pt 44.80. Found: C 36.03, H 5.52, N 6.32, Pt 44.37.

N,N'-(2-(2',3'-dihydroxypropyloxymethyl)-2-methyl-1,3-propanediamine)platinum(II) N-(carbamoylmethyl)-iminodi-acetate (compound 33)

Compound 33 is prepared starting from compound 26.
Elemental analysis: Calc.: C 29.21, H 4.90, N 9.73, Pt 33.20. Found: C 29.23, H 4.91, N 9.63, Pt 32.97.

N,N'-(2-(2'-hydroxy-3'-methoxypropyloxymethyl)-2-methyl-1,3-propanediamine)platinum(II)
1,1-cyclobutanedicarboxylate (compound 34)

Compound 34 was prepared starting from compound 28.
Elemental analysis: Calc.: C 33.14, H 5.19, N 5.15, Pt 35.90. Found: C 32.06, H 5.07, N 5.12, Pt 35.63.

N,N'-(2-(β-O-glucopyranosyloxymethyl)-2-methyl-1,3-propanediamine)platinum(II) malonate (compound 35)

Compound 35 was prepared starting from compound 29.
Elemental analysis: Calc.: C 29.11, H 4.53, N 4.85, Pt 33.80. Found: C 29.05, H 4.50, N 4.73, Pt 33.22.

Example 5

Determination of the cytostatic activity

The cytostatic activity of the compounds according to the invention is determined on L1210 leukemia cells of the mouse. In detail, the following test systems were used:

a) Colonization by L1210 leukemia cells in soft agar

This method is used to detect an influence of the test substances on the growth behaviour of the cells over several generations (at a cell cycle time of 10–12 hours, about 14 subsequent generations were observed in the test time of 7 days). In this test cytostatically active substances cause the number of colonies observed to be reduced compared to an untreated control. In detail, the test is carried out as follows:

500 leukemia cells per plate are incubated for 1 hour at 37° C. with different concentrations of the test substance. The cells are subsequently washed twice with McCoy 5A medium and finally poured out into petri dishes after adding 0.3% of agar. Controls are incubated only with fresh medium. Instead of incubating for one hour, different concentrations and test substances are in many cases mixed with the upper agar layer in order to thus achieve continuous exposition of the cells over the entire incubation time. After solidification of the agar, the plates are incubated in an incubator for 7 days at 37° C. (5% by volume of CO$_2$, 95% relative atmospheric humidity). The number of colonies produced with a diameter of more than 60 μm is subsequently counted. The results are given as the number of colonies in the treated agar plate, in per cent of the untreated control. From the dose-action curve thus attained, the IC$_{50}$ is determined as a measure of the activity of the substance. The results of the tests compared to Cisplatin are collated in Table 1.

b) Determination of the acute toxicity

In order to determine the acute toxicity, NMRI mice are injected intraperitoneally on day 0 with various doses of a test substance, dissolved in 0.5 ml of 5% glucose solution. Control groups receive only 0.5 ml of 5% strength glucose solution. 5 mice are used per concentration of the test substance. On day 14, the number of surviving mice is determined, and the LD5, LD50 and LD95 are determined from this according to the Lichtfield Wilcoxon method. The toxicity (LD$_{50}$ (mg/kg)) of the compounds described here are collated in Table 1 compared to cisplatin.

c) In vivo activity of the platinum complexes against L1210 leukemia of the mouse Ascitic fluid is removed under sterile conditions from DBA2 mice (female, 18–20 g) 7 days after implantation. The ascites is washed three times with PBS, counted, and adjusted to a cell number of 10$^6$ in 0.2 ml of PBS.

10$^6$ cells, suspended in 0.2 ml of PBS, are subsequently injected intraperitoneally into DBF1 mice (female, 18–20 g). 6 animals per group are employed for each substance concentration or as control.

Determination of the antitumoral activity a) The animals are weighed on days 1 and 5 after injection of the test substance. A weight loss of more than 20% on day 5 is regarded as an indicator of a toxic substance action.

b) At the end of the experiment (death of all animals or surviving animals on day 60), the mean survival time of the animals in each group is determined, so long as at least 65% of the animals were still living on day 5 of the experiment. The average survival time is determined exclusively for animals dying during the experiment. Long-term survivors (LTS) are not taken into account in this calculation and are specified separately.

From the mean survival time (MST) of the untreated group and of the control group ($MST_C$), the antitumoral activity (T/C) for each substance concentration is determined in per cent of the untreated control from the following formula:

$$T/C\ \% = \frac{MST_T}{MST_C} \times 100$$

T/C values of greater than 125% are regarded as an indicator of a significant antitumoral activity of the test substance. The dose which causes the greatest antitumoral effect (optimal dosage) and in each case one dose step above and below this dose are collated in Table 1. Animals which are still living on day 60 of the experiment are listed separately as "long-term survivors".

Treatment program:

The treatment program employed in each of the different experiments is given in Table 1.

TABLE 1

| Compound No.: | $IC_{50}$ (µg/ml) | $LD_{50}$ (mg/kg); 1 × i.p. | Treatment program | T/C % (optimum Dose/LTS*) L1210 |
|---|---|---|---|---|
| 11 | 1.4 | — | — | — |
| 12 | 0.5 | 19 | 3 × i.p./i.p. | 227 (3/—) |
| 13 | 1.25 | 57.3 | 5 × i.p./i.p. | 156 (8/—) |
| 14 | 0.75 | 57.1 | 3 × i.p./i.p. | 168 (4/—) |
| 15 | 2.9 | 1–5 | — | — |
| 17 | 1.1 | 50–100 | 3 × i.p./i.p. | 113 (30/—) |
| 30 | 1.4 | — | — | — |
| 31 | 2.6 | 250 | 2 × i.p./i.p. | 226 (112/3/6) |
| 32 | 3.6 | 437 | 5 × i.p./i.p. | 194 (47, 4/—) |
| Cis-platin | 0.04 | 14 | 3 × i.p./i.p. | 157 (4/—) |

LTS* = Long-term survivor

The solubility of the platinum complexes according to the invention is given in Table 2 compared to cis-diamminedichloroplatinum (II).

TABLE 2

| Compound No. | Solubility in water (mg/ml) |
|---|---|
| 11 | 3 |
| 13 | 25 |
| 14 | 16 |
| 15 | 17 |
| 17 | 10 |
| 30 | 18 |
| 31 | 15 |
| 32 | 70 |
| cis-diamminedichloro-platinum (II) | 1 |

We claim:

1. A compound of the formula I

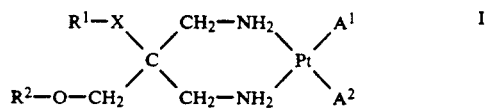

in which:
R¹ represents a hydrogen atom or an alkyl group of the formula $CH_3(CH_2)_n$—where n is 0, 1, 2, 3, 4 or 5;
R² represents a hydrogen atom when X is a carbamoyl group, an alkyl group having 1 to 6 carbon atoms, a group of the formula $R^3$—O—CH$_2$—(CHR$^4$)$_m$—CH$_2$—in which:
  R³ is a hydrogen atom or an alkyl group having 1 to 6 carbon atoms,
  R⁴ is a hydroxyl group or an alkyloxy group having 1 to 3 carbon atoms, and
  m is 0, 1 or 2,
a group of the formula H—(CH$_2$)$_a$—(O—(CH$_2$)$_b$)$_c$—where a is 0, 1, 2, 3 or 4, b is 1, 2, 3 or 4 and c is 1, 2, 3, 4, 5, 6 or 7, or a radical of the formula

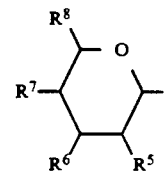

in which:
R⁵, R⁶ and R⁷, independently of one another, are a hydrogen atom or a hydroxyl group, and
R⁸ is a hydrogen atom, a methyl group or a hydroxy methyl group;
X represents a methylene group, a carbamoyl group or a covalent bond between R¹ and the 2-carbon atom; and
A¹ and A² are identical and represent a hydroxyl group, chloride, bromide, iodide, nitrate, acetate or trifluoroacetate, or A¹ represents sulfate or carbonate and A² represents H$_2$O, or A¹ and A² together represent the dianion of an organic acid.

2. A compound of the formula II, which is useful as a precursor for the preparation of a compound as claimed in claim 1,

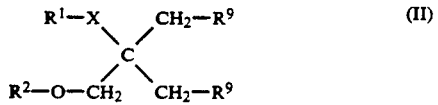

in which:
R¹ is a hydrogen atom or an alkyl group of the formula $CH_3(CH_2)_n$ where n is 0, 1, 2, 3, 4 or 5,
R² is a hydrogen atom,
R⁹ is an azide group, and
X is a methylene group, a carbamoyl group or a covalent bond between R¹ and the 2-carbon atom.

3. A compound of the formula II, which is useful as an intermediate for the preparation of a compound as claimed in claim 1,

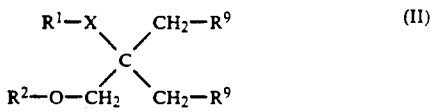 (II)

in which:
R1 represents a hydrogen atom or an alkyl group of the formula CH$_3$(CH$_2$)n—where n is 0, 1, 2, 3, 4 or 5;
R2 represents a hydrogen atom when X is a carbamoyl group, an alkyl group having 1 to 6 carbon atoms, a group of the formula R$^3$—O—CH$_2$—(CHR$^4$)$_m$-CH$_2$—in which:
R3 is a hydrogen atom or an alkyl group having 1 to 6 carbon atoms,
R4 is a hydroxyl group or an alkyloxy group having 1 to 3 carbon atoms, and
m is 0, 1 or 2,
a group of the formula H—(CH$_2$)$_a$—(O—(CH$_2$)$_b$-)$_c$—where a is 0, 1, 2, 3 or 4, b is 1, 2, 3 or 4, and c is 1, 2, 3, 4, 5, 6 or 7, or a radical of the formula

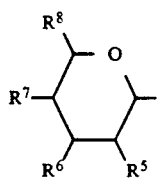

in which:
R5, R6 and R7, independently of one another, are a hydrogen atom or a hydroxyl group, and
R8 is a hydrogen atom, a methyl group or a hydroxy methyl group;
X represents a methylene group, a carbamoyl group or a covalent bond between R$^1$ and the 2-carbon atom; and
R$^9$ denotes an azido group, an amino group, or an ammonium salt.

4. A process for the preparation of a compound as claimed in claim 1, comprising reacting K$_2$PtCl$_4$ with a diamino compound of the formula II

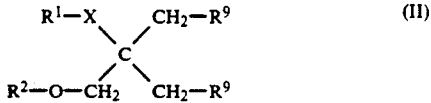 (II)

in which:
R1 represents a hydrogen atom or an alkyl group of the formula CH$_3$(CH$_2$)n—where n is 0, 1, 2, 3, 4 or 5;
R2 represents a hydrogen atom when X is a carbamoyl group, an alkyl group having 1 to 6 carbon atoms, a group of the formula R$^3$—O—CH$_2$—(CHR$^4$)$_m$—CH$_2$—in which:
R3 is a hydrogen atom or an alkyl group having 1 to 6 carbon atoms,
R4 is a hydroxyl group or an alkyloxy group having 1 to 3 carbon atoms, and
m is 0, 1 or 2,
a group of the formula H—(CH$_2$)$_a$—(O—(CH$_2$)$_b$-)$_c$—where a is 0, 1, 2, 3 or 4, b is 1, 2, 3 or 4, and c is 1, 2, 3, 4, 5, 6 or 7, or a radical of the formula

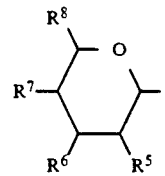

in which:
R5, R6 and R7, independently of one another, are a hydrogen atom or a hydroxyl group, and
R8 is a hydrogen atom, a methyl group or a hydroxy methyl group;
X represents a methylene group, a carbamoyl group or a covalent bond between R$^1$ and the 2-carbon atom; and
R$^9$ denotes an azido group, an amino group, or an ammonium salt.

5. A compound as recited in claim 1, wherein A$^1$ and A$^2$ together represent the dianion of an organic acid selected from the group consisting of oxalic, malonic, hydroxymalonic, ethylmalonic, 1,1-cyclobutanedicarboxylic, 1,2-cyclobutanedicarboxylic, phthalic, 3-carboxyphthalic, 4-carboxyphthalic, 3,4-dicarboxyphthalic, and n-(carboylmethyl)-iminodiacetic acid.

6. A compound as recited in claim 1, wherein:
R$^1$ is a methyl or ethyl group;
R$^2$ is a methyl or ethyl group, a group of the formula

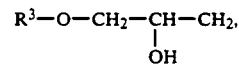

or a group of the formula R$^3$—(OCH$_2$CH$_2$)c— where R$^3$ is a hydrogen atom or a methyl radical, and c is 1, 2, 3, or 6, or a radical of the formula

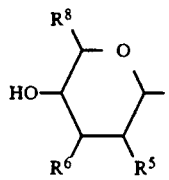

where:
R$^5$ and R$^6$, independently of one another, are a hydrogen atom or a hydroxyl group, and
R$^8$ is a hydrogen atom, a methyl group or a hydroxymethyl group;
X is a covalent bond; and
A$^1$ and A$^2$ are identical and are a hydroxyl group, chloride or nitrate, or together are the dianion of malonic, 1,1-cyclobutanedicarboxylic or N-(carbamoylmethyl)-iminodiacetic acid.

7. A compound as recited in claim 1, wherein
R$^1$—X is an acetamido group;
R$^2$ is a hydrogen atom; and
A$^1$ and A$^2$ are identical and are a hydroxyl group, chloride, or nitrate, or together are the dianion of malonic, 1,1-cyclobutanedicarboxylic or N-(carbamoylmethyl)iminodiacetic acids.

8. A medicament useful in the treatment of tumors comprising, a compound of the formula

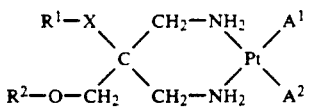

in which:
R$^1$ represents a hydrogen atom or an alkyl group of the formula CH$_3$(CH$_2$)$_n$- where n is 0, 1, 2, 3, 4 or 5;
R$^2$ represents a hydrogen atom when X is a carbamoyl group, an alkyl group having 1 to 6 carbon atoms, a group of the formula R$^3$—O—CH$_2$—(CHR$^4$)$_m$—CH—in which:
R$^3$ is a hydrogen atom or an alkyl group having 1 to 6 carbon atoms,
R$^4$ is a hydroxyl group or an alkyloxy group having 1 to 3 carbon atoms, and
m is 0, 1 or 2,
a group of the formula H—(CH$_2$)$_a$—(O—(CH$_2$)$_b$-)$_c$—where a is 0, 1, 2, 3 or 4, b is 1, 2, 3 or 4 and c is 1, 2, 3, 4, 5, 6 or 7, or a radical of the formula

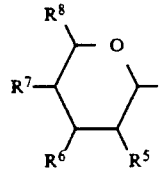

in which:
R$^5$, R$^6$ and R$^7$, independently of one another, are a hydrogen atom or a hydroxyl group, and
R$^8$ is a hydrogen atom, a methyl group or a hydroxy methyl group;
X represents a methylene group, a carbamoyl group or a covalent bond between R$^1$ and the 2-carbon atom; and
A$^1$ and A$^2$ are identical and represent a hydroxyl group, chloride, bromide, iodide, nitrate, acetate or trifluoroacetate, or A$^1$ represents sulfate or carbonate and A$^2$ represents H$_2$O, or A$^1$ and A$^2$ together represent the dianion of an organic acid;
together with a pharmaceutically acceptable diluent or carrier.

9. A medicament for the treatment of tumors as recited in claim 8, wherein A$_1$ and A$_2$, together represent the dianion of an organic acid selected from the group consisting of oxalic, malonic, hydroxymalonic, ethylmalonic, 1,1-cyclobutanedicarboxylic, 1,2-cyclobutanedicarboxylic, phthalic, 3-carboxyphthalic, 4-carboxyphthalic, 3,4-dicarboxyphthalic, and n-(carbamoylmethyl)-iminodiacetic acid.

10. A medicament for the treatment of tumors as recited in claim 8, wherein:
R$^1$ is a methyl or ethyl group;
R$^2$ is a methyl or ethyl group, a group of the formula

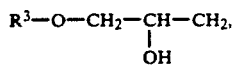

or a group of the formula R$^3$—(OCH$_2$CH$_2$)$_c$—where R$^3$ is a hydrogen atom or a methyl radical, and c is 1, 2, 3, or 6, or a radical of the formula

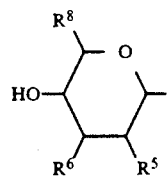

where:
R$^5$ and R$^6$, independently of one another, are a hydrogen atom or a hydroxyl group, and
R$^8$ is a hydrogen atom, a methyl group or a hydroxylmethyl group;
X is a covalent bond; and
A$^1$ and A$^2$ are identical and are a hydroxyl group, chloride or nitrate, or together are the dianion of malonic, 1,1-cyclobutanedicarboxylic or N-(carbamoylmethyl)-iminodiacetic acid.

11. A method for the treatment of tumors comprising administering to a patient having tumors an effective amount of a compound of the formula

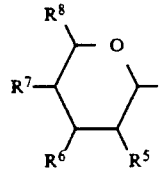

in which:
R$^1$ represents a hydrogen atom or an alkyl group of the formula CH$_3$(CH$_2$)$_n$—where n is 0, 1, 2, 3, 4 or 5;
R$^2$ represents a hydrogen atom when X is a carbamoyl group, an alkyl group having 1 to 6 carbon atoms, a group of the formula R$^3$—O—CH$_2$—(CHR$^4$)$_m$—CH$_2$—in which:
R$^3$ is a hydrogen atom or an alkyl group having 1 to 6 carbon atoms,
R$^4$ is a hydroxyl group or an alkyloxy group having 1 to 3 carbon atoms, and
m is 0, 1 or 2,
a group of the formula H—(CH$_2$)$_a$—(O—(CH$_2$)$_b$-)$_c$—where a is 0, 1, 2, 3 or 4, b is 1, 2, 3 or 4 and c is 1, 2, 3, 4, 5, 6 or 7, or a radical of the formula

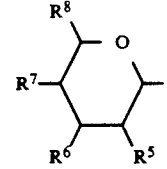

in which:
R$^5$, R$^6$ and R$^7$, independently of one another, are a hydrogen atom or a hydroxyl group, and
R$^8$ is a hydrogen atom, a methyl group or a hydroxy methyl group;
X represents a methylene group, a carbamoyl group or a covalent bond between R$^1$ and the 2-carbon atom; and
A$^1$ and A$^2$ are identical and represent a hydroxyl group, chloride, bromide, iodide, nitrate, acetate or trifluoroacetate, or A$^1$ represents sulfate or carbonate and A$^2$ represents H$_2$O, or A$^1$ and A$^2$ together represent the dianion of an organic acid.

12. A method for the treatment of tumors as recited in claim 11, wherein $A^1$ and $A^2$ together represent the dianion of an organic acid selected from the group consisting of oxalic, malonic, hydroxymalonic, ethylmalonic, 1,1-cyclobutanedicarboxylic, 1,2-cyclobutanedicarboxylic, phthalic, 3-carboxyphthalic, 4-carboxyphthalic, 3,4-dicarboxyphthalic, and n-(carbamoylmethyl)-iminodiacetic acid.

13. A method for the treatment of tumors as recited in claim 11, wherein:

$R^1$ is a methyl or ethyl group;

$R^2$ is a methyl or ethyl group, a group of the formula

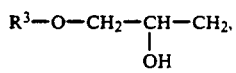

or a group of the formula $R^3-(OCH_2CH_2)_c-$ where $R^3$ is a hydrogen atom or a methyl radical, and c is 1, 2, 3, or 6, or a radical of the formula

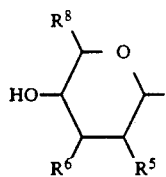

where:

$R^5$ and $^6$, independently of one another, are a hydrogen atom or a hydroxyl group, and $R^8$ is a hydrogen atom, a methyl group or a hydroxymethyl group;

X is a covalent bond; and $A^1$ and $A^2$ are identical and are a hydroxyl group, chloride or nitrate, or together are the dianion of malonic, 1,1-cyclobutanedicarboxylic or N-(carbamoylmethyl)-iminodiacetic acid.

UNITED STATES PATENT AND TRADEMARK OFFICE
CERTIFICATE OF CORRECTION

PATENT NO. : 5,091,521
DATED : February 25, 1992
INVENTOR(S) : Cenek Kolar et al.

It is certified that error appears in the above-identified patent and that said Letters Patent is hereby corrected as shown below:

Abstract, last line, change "containg" to --containing--.
Claim 3, column 15, line 8, change "R1" to --$R^1$--.
Claim 3, column 15, line 11, change "R2" to --$R^2$--.
Claim 3, column 15, line 15, change "R3" to --$R^3$.
Claim 3, column 15, line 17, change "R4" to --$R^4$--.
Claim 3, column 15, line 34, change "R5,R6, and R7" to --$R^5, R^6$ and $R^7$.
Claim 3, column 15, line 36, change "R8" to --$R^8$.
Claim 4, column 54, change "R1" to --$R^1$--.
Claim 4, column 15, line 57, change "R2" to --$R^2$--.
Claim 4, column 15, line 61, change "R3" to --$R^3$--.
Claim 4, column 15, line 63, change "R4" to --$R^4$--.
Claim 4, column 16, line 11, change "R5,R6, and R7" to --$R^5, R^6$ and $R^7$.
Claim 4,, column 16, line 13, change "R8" to --$R^8$--.
Claim 5, column 16, line 27, change "(carboylmethyl)" to --carbamoylmethyl)--.
Claim 9, column 17, line 49, change "$A_1$ and $A_2$" to --$A^1$ and $A^2$--.
Claim 10, column 18, lines 13 and 14, change "hydroxylmethyl" to --hydroxymethyl--.

UNITED STATES PATENT AND TRADEMARK OFFICE
CERTIFICATE OF CORRECTION

Page 2 of 2

PATENT NO. : 5,091,521
DATED : February 25, 1992
INVENTOR(S) : Cenek Kolar, et. al.

It is certified that error appears in the above-indentified patent and that said Letters Patent is hereby corrected as shown below:

Claim 13, column 20, line 13, change "$^6$" to $R^6$--.

Signed and Sealed this

Nineteenth Day of October, 1993

Attest:

BRUCE LEHMAN

Attesting Officer     Commissioner of Patents and Trademarks